US008984731B2

(12) United States Patent
Broeck et al.

(10) Patent No.: US 8,984,731 B2
(45) Date of Patent: Mar. 24, 2015

(54) GUIDES WITH PRESSURE POINTS

(71) Applicant: Materialise N.V., Leuven (BE)

(72) Inventors: Joyce Van Den Broeck, Kessel-Lo (BE); Nele Daemen, Bonheiden (BE); Katerina Nikonenko, Kiev (UA); Maryna Stepanenko, Kyiv (UA)

(73) Assignee: Materialise N.V., Leuven (BE)

( * ) Notice: Subject to any disclaimer, the term of this patent is extended or adjusted under 35 U.S.C. 154(b) by 0 days.

(21) Appl. No.: 14/263,932

(22) Filed: Apr. 28, 2014

(65) Prior Publication Data

US 2014/0230215 A1    Aug. 21, 2014

Related U.S. Application Data

(63) Continuation of application No. PCT/EP2012/071258, filed on Oct. 26, 2012.

(60) Provisional application No. 61/552,510, filed on Oct. 28, 2011.

(30) Foreign Application Priority Data

Oct. 28, 2011   (EP) .................................... 11187145

(51) Int. Cl.
| | |
|---|---|
| *B23Q 17/00* | (2006.01) |
| *A61B 19/00* | (2006.01) |
| *A61B 17/17* | (2006.01) |
| *A61F 2/30* | (2006.01) |

(Continued)

(52) U.S. Cl.
CPC .............. *A61B 19/50* (2013.01); *A61B 17/1739* (2013.01); *A61F 2/30* (2013.01); *A61B 17/17* (2013.01); *A61B 17/68* (2013.01); *A61F 2/28* (2013.01); *A61F 2/30942* (2013.01); *A61B 2017/0042* (2013.01); *A61B 2017/00526* (2013.01); *A61B 2017/1778* (2013.01); *A61B 2017/568* (2013.01); *A61B 2017/90* (2013.01);

(Continued)

(58) Field of Classification Search
USPC ........... 29/407.01, 407.08, 408.09; 506/86 R, 506/87, 88, 96; 606/86 R, 87, 88, 96
See application file for complete search history.

(56) References Cited

U.S. PATENT DOCUMENTS

| 5,141,680 A | 8/1992 | Almquist |
| 2007/0233129 A1 | 10/2007 | Bertagnoli |

(Continued)

FOREIGN PATENT DOCUMENTS

| EP | 1586270 A2 | 10/2005 |
| EP | 2208470 A1 | 7/2010 |

(Continued)

OTHER PUBLICATIONS

Intl. Search Report issued Apr. 1, 2013 on related application PCT/EP2012/071258, filed Oct. 26, 2012.

(Continued)

*Primary Examiner* — John C Hong
(74) *Attorney, Agent, or Firm* — EIP US LLP

(57) ABSTRACT

The application provides methods for providing a surgical guide for placement on an anatomical part wherein the guide is provided with one or more dedicated push features that can be used as pressure points for applying force onto the surgical guide. The application further provides guides comprising one or more push features which can be used as a pressure point for applying force onto said guide.

15 Claims, 7 Drawing Sheets

(51) Int. Cl.
    *A61B 17/68*     (2006.01)
    *A61F 2/28*     (2006.01)
    *A61F 2/46*     (2006.01)
    *A61B 17/00*     (2006.01)
    *A61B 17/56*     (2006.01)
    *A61B 17/90*     (2006.01)
    *A61B 17/15*     (2006.01)

(52) U.S. Cl.
    CPC ............ *A61B 17/155* (2013.01); *A61B 17/157* (2013.01); *A61B 2019/508* (2013.01)
    USPC ...................................... 29/407.01; 606/86 R

(56) References Cited

U.S. PATENT DOCUMENTS

| | | |
|---|---|---|
| 2009/0088760 A1 | 4/2009 | Aram |
| 2009/0254093 A1 | 10/2009 | White |
| 2011/0015636 A1 | 1/2011 | Katrana |
| 2011/0087332 A1 | 4/2011 | Bojarski |
| 2011/0160867 A1 | 6/2011 | Meridew |
| 2012/0151730 A1* | 6/2012 | Fitz et al. .................. 29/407.01 |
| 2012/0289965 A1* | 11/2012 | Gelaude et al. ................. 606/87 |
| 2014/0058466 A1* | 2/2014 | Keppler et al. ............. 606/86 R |

FOREIGN PATENT DOCUMENTS

| | | |
|---|---|---|
| WO | 2011029911 A1 | 3/2011 |
| WO | 2011106399 A1 | 9/2011 |

OTHER PUBLICATIONS

Intl. Preliminary Report on Patentability issued Feb. 14, 2014 on related application PCT/EP2012/071258, filed Oct. 26, 2012.

* cited by examiner

A

B

GUIDES WITH PRESSURE POINTS

CROSS-REFERENCE TO RELATED APPLICATIONS

This application is a continuation under 35 U.S.C. §120 of International Application No. PCT/EP2012/071258, filed Oct. 26, 2012 (and published by the International Bureau as International Publication No. WO 2013/060842 on May 2, 2013), which claims the benefit of U.S. Provisional Patent Application No. 61/552,510, filed Oct. 28, 2011, and which also claims priority to European Application No. 11187145.5, filed Oct. 28, 2011. Each of the above referenced patent applications is hereby incorporated by reference in its entirety.

BACKGROUND OF THE INVENTION

The present application relates to methods for providing surgical guides for placement on an anatomical part, wherein the guide is provided with one or more dedicated push features that can be used to apply force onto the surgical guide.

Conventional orthopedic prostheses and implants, such as knee and hip implant systems, have been in use for many years with considerable success. Moreover, the use of custom designed prostheses and implant components based on patient-specific anatomy has overcome many shortcomings of the older designs. Such patient-specific devices can be developed using commercially available software. Typically such devices are used for orthopedic interventions to the spine, hip, knee and/or radius. Patient-specific devices available on the market include patient-specific knee replacement prostheses, patient-specific femoral and tibia cutting blocks, distal radius drilling, cutting templates, etc. At present, there exists an increasing number of surgical interventions that benefit from the use of these medical image based patient specific surgical devices as described, for instance, in patent publications US 2005/0203528 A1 and EP 1486900 A1.

While patient-specific devices such as guides are now used to accurately place pins, guide bone cuts or insert implants during orthopedic procedures, the correct positioning of these patient-specific devices remains a critical factor with an important impact on the outcome of the procedure.

The actual placement and maintenance of the patient-specific device in the correct position is not always straightforward for the operator, leading to uncertainty for the operator and possible incorrect placement of the patient-specific device and thus deviations from the surgical planning. As the best orthopedic results are achieved when the procedure occurs under the best circumstances, i.e. not only the device being correctly positioned but also the operator being assured about the correct position of the patient-specific device, there is a need in the art for devices which make it possible to ensure correct positioning of the patient-specific device. Also it is desirable that the operator is assured of the fact that the patient-specific device is maintained in the correct position during the procedure.

SUMMARY

The application provides patient-specific devices which comprise one or more push features that allow the operator to ensure correct positioning of the device. The application further provides methods for providing patient-specific devices including one or more features that can be used as a mechanism for applying force onto the patient-specific device. By precisely positioning said features on said patient-specific devices, the resulting patient-specific devices comprise a feature that allow the user to specifically and correctly position the patient-specific device onto a pre-defined location. The resulting patient-specific devices also allow the operator to maintain the position of a patient-specific device in the correct pre-defined location without any major additional burden for the operator.

Provided herein are methods for obtaining a patient-specific device for placement on an anatomical part, wherein the methods comprise the steps of: a) determining the areas on the anatomical part which can be used in the design of one or more contact surfaces for a patient-specific device to be placed thereon; b) determining from said one or more contact surfaces the axis of least-constrained rotational direction and/or the axis of least-constrained translational direction of said patient-specific device on said anatomical part; and c) designing said patient-specific device with one or more push features that can be used as a mechanism for applying force onto said patient-specific device; wherein said one or more push features are designed such that a force applied thereto is perpendicular to the axis of least-constrained rotational direction and/or parallel to the axis of least-constrained translational direction of movement of the patient-specific device on said anatomical part.

In a particular embodiment, said push feature is a button, finger-pit, handle or grip. More particularly, said push feature is spring-loaded, which is reactive to a predetermined pressure applied thereto.

In a particular embodiment said patient-specific device is provided with two or more push features. The provision of more than one push feature may allow the user to apply additional force spread over the contact surface of the patient-specific device. Multiple functional elements can also allow the user to choose the push feature at the location that maximizes the ease of use.

In a particular embodiment said patient-specific device is a surgical patient-specific device. More particularly, said patient-specific device is a guide, prosthesis or implant.

In a particular embodiment one or more of the contact surfaces are patient-specific.

In a particular embodiment the method further comprises the step of manufacturing said patient-specific device or part thereof through additive manufacturing.

Further provided herein are patient-specific devices, such as those obtainable by the methods described herein.

More particularly, provided herein are patient-specific devices comprising a body with one or more contact surfaces for positioning on an anatomical part, wherein the body further comprises one or more push features which can be used as a mechanism for applying force onto the patient-specific device. More particularly the one or more features are designed such that the force applied thereto is perpendicular to the axis of least-constrained rotational direction and/or parallel to the axis of least-constrained translational direction of the patient-specific device on said anatomical part.

In a particular embodiment one or more of said contact surfaces of the patient-specific devices are patient-specific.

In a particular embodiment said device comprises a push feature which is selected from a button, finger-pit, handle or grip.

In a particular embodiment the patient-specific device is a surgical patient-specific device. More particularly, said patient-specific device is a guide, prosthesis or implant. In a particular embodiment the patient-specific device is provided with two or more push features.

BRIEF DESCRIPTION OF THE DRAWINGS

The following description of the figures of specific embodiments of the methods and devices described herein is merely exemplary in nature and is not intended to limit the present teachings, their application or uses. Throughout the drawings, corresponding reference numerals indicate like or corresponding parts and features.

Figure 1:
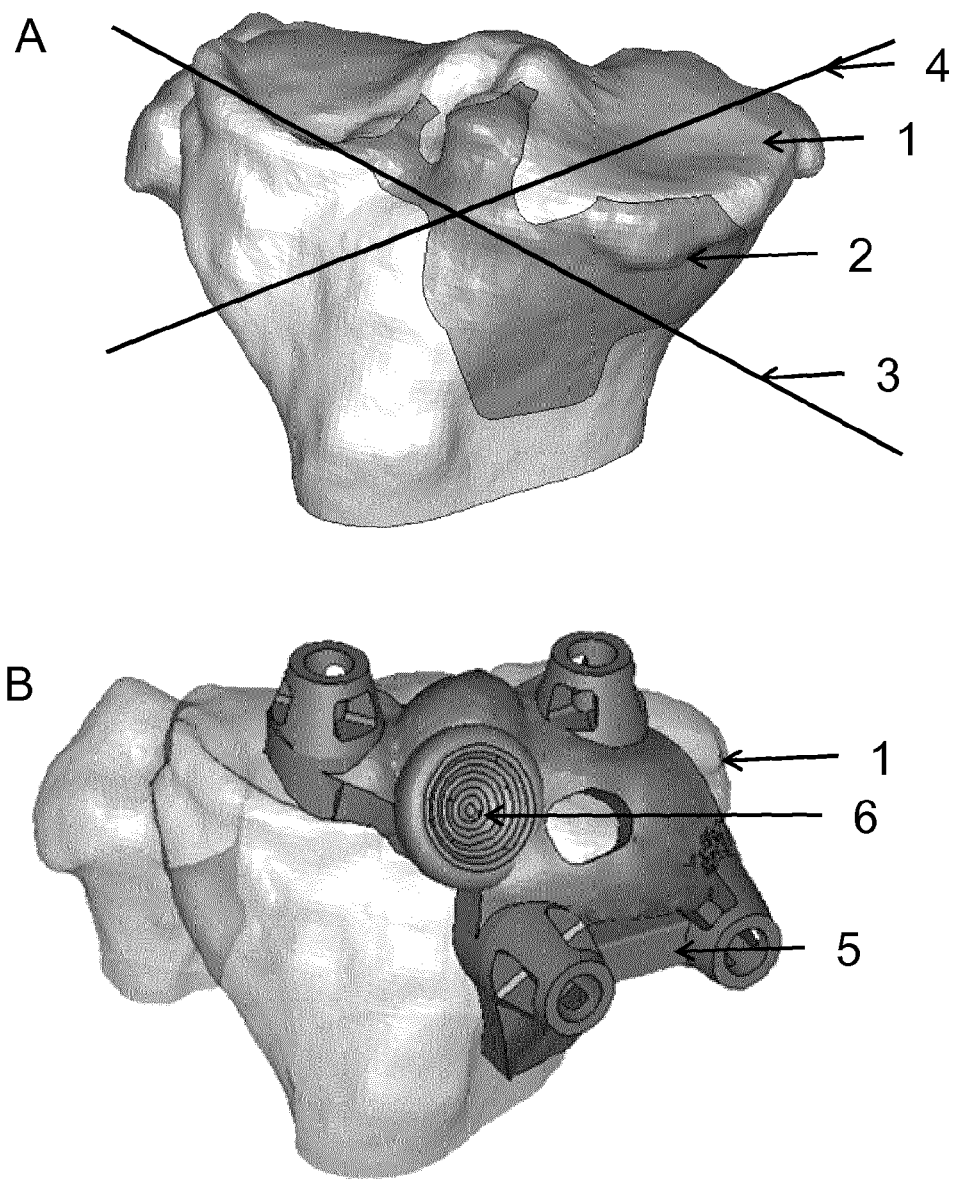
FIG. 1 (A-B): Illustration of the different steps in the method for designing a patient-specific device as envisioned herein.

In the Figures, the following numbering is used: 1—anatomical part; 2—contact surface; 3—axis of least-constrained rotational direction; 4—axis of least-constrained translational direction; 5—patient-specific device; 6—push feature; 7—support structure; 8—guiding feature.

DETAILED DESCRIPTION OF CERTAIN INVENTIVE EMBODIMENTS

Before the present method and devices provided herein are described, it is to be understood that the teachings herein are not limited to particular methods, components, or devices described, as such methods, components, and devices may, of course, vary. It is also to be understood that the terminology used herein is not intended to be limiting, since the scope of the teachings herein will be limited only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments described herein are capable of operation in other sequences than described or illustrated herein.

The term "about" as used herein when referring to a measurable value such as a parameter, an amount, a temporal duration, and the like, is meant to encompass variations of +/−10% or less, preferably +1-5% or less, more preferably +/−1% or less, and still more preferably +/−0.1% or less of and from the specified value, insofar as such variations are appropriate to perform as described. It is to be understood that the value to which the modifier "about" refers is itself also specifically, and preferably, disclosed. The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used herein, including technical and scientific terms, have the meaning as commonly understood by one of ordinary skill in the art to which the devices and methods described herein belong. By means of further guidance, definitions for the terms used in the description are included to better appreciate the present teachings. The terms or definitions used herein are provided solely to aid in the understanding of the teachings provided herein. Although any methods and materials similar or equivalent to those described herein may be used in the practice or testing of methods and devices described herein, the preferred methods and materials are described herein.

Reference throughout this specification to "one embodiment" or "an embodiment" means that a particular feature, structure or characteristic described in connection with the embodiment is included in at least one embodiment as envisioned herein. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the teachings provided herein, and form different embodiments, as would be understood by those in the art. For example, in the following claims, any of the claimed embodiments can be used in any combination.

Described herein are methods of evaluating guide stability and, providing patient-specific devices comprising features such as push features that can be used for applying a force onto said devices. By precisely positioning said features onto said patient-specific devices these features allow the user to specifically and correctly position the patient-specific device onto the pre-defined location. The patient-specific devices comprising the push features described herein may also allow the operator to maintain the position of a patient-specific device in the correct pre-defined location without any major additional burden for the operator.

As used herein, the term "patient-specific device" relates to any surgical, therapeutic or diagnostic device or tool such as an implant, a prosthesis or a surgical guide which is designed based on an individual patient's anatomy to include features which have a custom fit and/or to perform a customized function for a specific patient. The use of guides and implants which are patient-specific makes it possible to ensure an improved or optimized accuracy of the surgical intervention and an improved anatomical fit for prosthetic structures thereby ensuring optimized functionality for each patient. Even when such devices are used in combination with standard implants, tools, devices, surgical procedures, or other methods, important benefits in accuracy of placement can be obtained.

Importantly, the methods described herein can be used for providing or improving any type of patient-specific device that requires accurate positioning on any type of organic tissues such as bone, teeth, cartilage or skin. In particular, the patient-specific devices with push features described herein can be used for orthopedic interventions to the shoulder, spine, hip, and knee. Accordingly, the term "patient-specific device" is used to refer to a custom-made device specific to the individual patient's anatomy.

The features which have a custom fit or perform a customized function for a specific patient may also be referred to herein as the "patient-specific element".

In a first aspect, the methods described herein allow for providing a patient-specific device for placement on an anatomical part, by providing a patient-specific device with one or more push features. The location of a push feature on the patient specific device can be determined by an analysis of stability. As a result, devices can be designed with one or more push features such that the application of a force on a push feature can help ensure correct positioning and stability of the device. To do this, the desired direction of orientation of the device on the anatomical part needs to be determined. This is ensured by determining the axis of least-constrained rotational direction or the axis of least-constrained translational direction of the patient-specific device on the anatomical part, or both. In particular embodiments, this is derived from the parts of the device which ensure the contact with the anatomical part.

Thus, contact surfaces of a patient-specific device can be determined which allow the device to fit specifically onto the anatomical part of the patient. Based on a stability analysis thereof the location of a push feature can be determined which will allow to optimize positioning and stability of said patient-specific device.

In particular embodiments, the methods envisioned herein comprise the steps of: a) determining the areas on the anatomical part which can be used in the design of one or more contact surfaces for the patient-specific device; b) determining from said one or more contact surfaces the axis of least-constrained rotational direction or the axis of least-constrained translational direction of said patient-specific device on said anatomical part, or both; and c) providing (a digital model of) said patient-specific device with at least one (dedicated) push feature that can be used as a mechanism for applying force onto said improved patient-specific device; wherein said push feature or features ensures that a force applied thereto is perpendicular to the axis of least-constrained rotational direction or parallel to the axis of least-constrained translational direction of movement of the patient-specific device on said anatomical part, or both.

A first step thus comprises, determining, from the area of the body part for which surgical intervention is required, which areas will be used as contact surfaces. As used herein, the term "contact surface" relates to the areas on the patient-specific device that make contact with the anatomical part. The contact surfaces will typically be located around the area of intervention, i.e. around the location of an envisioned drill hole or cut. It will be understood that this step is performed based on three-dimensional images of the relevant area of the bone in combination with the pre-operative planning of the surgical intervention.

In particular embodiments, the methods envisioned herein may comprise the step of generating a three dimensional model of the patient's anatomy from medical images of the patient such as X-ray, Magnetic Resonance Imaging (MRI), Positron Emission Tomography (PET) scan, Computed Tomography (CT) scan or ultrasound images. Likewise, a patient-specific guide design can be determined based on, for example, the type of surgery to be performed.

Then, one or more contact surfaces can be determined based on images of the anatomical part of said patient, the three-dimensional model, and/or pre-operative planning of the surgical procedure. Typically, the contact surfaces of the device are patient-specific, i.e. the contact surfaces typically have a shape which is conformal with at least a part of a specific patient's anatomical part.

From the contact surfaces, the stability of the patient-specific device or guide when contacting the contact surfaces can be determined. The geometric information of the contact surfaces, including the vertex coordinates and unit outward normal vectors of the faces of the contact surfaces can be determined. This geometric information can then be used to characterize the stiffness of the contact between the guide and the anatomy. This stiffness can be understood to be the resistance the contact between the guide and the anatomy provides towards an externally applied force. The stiffness information can then serve as input for identifying the least-constrained direction of translation and rotation of the patient-specific device or guide on the anatomical part.

More particularly, the contact surface(s) between the patient-specific guide and the patient's anatomy is identified. Using the points defining this surface and their corresponding unit outward normal vectors, a spatial stiffness matrix of the contact is calculated. Using the eigenvalues of this stiffness matrix, information about the translational and rotational stiffness of the contact can be retrieved. The eigenvectors corresponding to the smallest eigenvalues will define the least-constrained axes of the contact surface.

In this way the least-constrained direction for a translation and/or rotation of the patient-specific device on the anatomical part is determined thereby identifying the optimal direction that force can be applied to the device upon positioning the device on the anatomical part. This will determine the position and orientation of the one or more push feature that is provided on the design of the patient-specific device.

Thus, in certain embodiments, a push feature can be included on the guide to restrict a possible straight movement over the least-constrained direction of translation. To do this, the force direction of the push feature should be oriented parallel to the least-constrained direction of translation. Similarly, a push feature can be added to the guide to restrict a likely rotation around the instantaneous axis of rotation defined by the least-constrained axis of rotation. The functional element should then be positioned such that the force direction is perpendicular to the least-constrained axis of rotation. Preferably, the position of the functional element is as far as possible from the location of instantaneous axis of rotation, to create a maximal restrictive moment applied on the guide.

In certain embodiments, the axis of least-constrained direction for rotation and translation can be determined using finite element analysis (see Example 4, below).

As used herein, the term "push feature" refers to a feature that is provided on the patient-specific devices according to the present methods wherein the push feature allows the user to apply force onto the patient-specific device. This allows the user to specifically and correctly position the patient-specific device onto the pre-defined location of the anatomical part. In particular embodiments, it further allows the operator to maintain the position of a patient-specific device in the correct pre-defined location without any major additional burden for the operator. In particular embodiments, the push feature can also be designed to enhance the application of a force by the user. Typically, the force is a manual force, more particularly a manual force which is created by the operator pushing on the device. The location and orientation of the push feature can be determined in such a way that application of a force thereto ensures stability of the device in the desired orientation. In particular embodiments, the push feature may be a dedicated push feature. In certain embodiments, the push feature may be a handle. In certain embodiments, the push feature may be designed to receive one or more fingers, more particularly finger tips. In further particular embodiments the push feature is a "finger pit".

Figure 7:
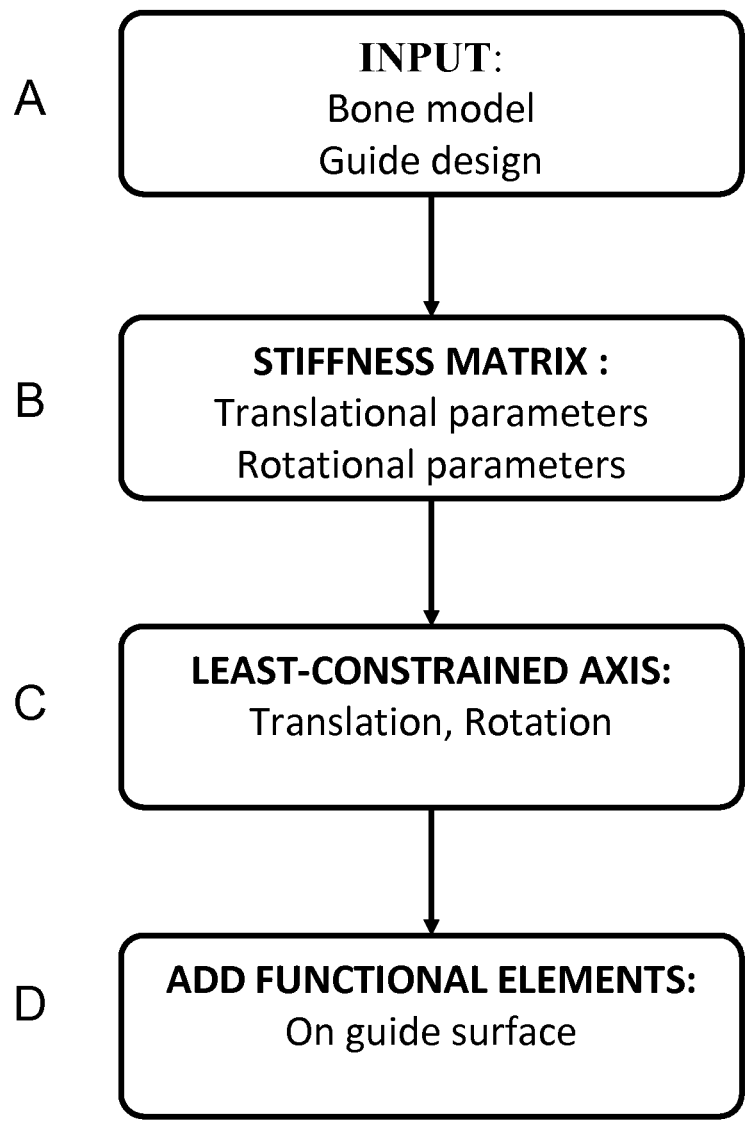
FIG. 7: Exemplary process for generating a patient-specific device with a push feature.

FIG. 7 illustrates an exemplary process for generating a patient-specific device with a push feature. At block A, the process generates the contact surfaces of an envisioned device on a three-dimensional model of the patient's anatomy generated from medical images. The three dimensional model may be based on medical images such as X-ray, MRI, PET-scan, CT-scan or ultrasound images. At block B, the process generates a stiffness matrix based on translational and rotational parameters. These parameters are determined by the geometric information of the contact surfaces. At block C, the process generates the least constrained axis of translation and/or rotation. Using the eigenvalues of the stiffness matrix, information about the translational and rotational stiffness of the contact can be retrieved. The eigenvectors corresponding to the smallest eigenvalues will define the least-constrained axes of the contact surface. At block D, the process further includes the provision of a push features to the patient-specific guide.

In some embodiments, it is envisioned that the force can be applied by way of a separate instrument or tool. In these embodiments, the push feature can be a dedicated feature which, when force is applied via an instrument or tool reversibly attached thereto, creates movement of the device in the desired orientation. Such an instrument can be a dedicated instrument. For example, the instrument or tool may be a handle and the push feature an aperture suitable for receiving the handle, wherein the orientation and location of the push feature is such that when force is applied to the handle connected to the patient-specific device via the push feature, the force is applied perpendicular to the axis of least-constrained rotational direction of movement of the guide on the anatomical part, parallel to the axis of least-constrained translational direction of movement of the patient-specific device on the anatomical part, or both.

In particular embodiments the push feature is provided as a support structure for a surgical tool. The term "surgical tool" as used herein relates to an element which is used during the surgical intervention and which can be positioned on the push feature of the patient-specific device or can be reversibly linked thereto for positioning and/or maintaining the patient-specific device in the correct position.

In particular embodiments of the methods described herein, the push feature can be a button, handle, grip or any functional feature that allows the user to apply a force. In certain embodiments of the method, the patient-specific device is provided with one, two, three, four or five push features wherein each or the combination of push feature(s) ensure(s) that a force applied thereto is perpendicular to the axis of least-constrained rotational direction and/or parallel to the axis of least-constrained translational direction of movement of the patient-specific device on said anatomical part.

In particular embodiments the methods described herein allow the provision of improved patient-specific devices, more particularly devices that require positioning on bone, with or without cartilage or other soft tissues.

In particular embodiments, the methods herein allow the provision of patient-specific devices that require positioning on soft tissue (such as tendons, ligaments, fascia, skin, fibrous tissues, fat, muscles or nerves) or cartilage. As inaccuracies in the positioning of patient-specific devices are a major problem when positioning a device on soft tissue or also for instance on cartilage, the provision of a push feature as described herein is particularly useful for accurately and precisely positioning a patient-specific device on soft tissue or cartilage.

While it will be clear to the skilled person that the methods described herein aim at optimizing the positioning of patient-specific devices, small deviations from the optimal position can be acceptable. Thus, in particular embodiments of the methods described herein, the position and orientation of the push features is such that it ensures that a force applied thereto is about perpendicular to the axis of least-constrained rotational direction and/or about parallel to the axis of least-constrained translational direction of movement of the patient-specific device on said anatomical part, wherein the degree of variation that is allowable for the direction in which the force is applied is smaller than 25°, more particularly smaller than 20°, more particularly smaller than 15°, more particularly smaller than 10°, more particularly smaller than 5° and most particularly smaller than 1°.

In particular embodiments, the one or more push features can be spring-loaded (i.e. loaded by means of a spring), which implies that they are reactive to a predetermined force applied thereto. This can be of interest e.g. to provide a signal (e.g. an auditive, sensitive and/or visual signal) to the user that the force has been or is being correctly applied. Thus, in particular embodiments, the application of a force to the push feature in the desired direction loads a spring which provides a sensitive signal to the user, i.e. the user can feel that the force has been applied.

In further particular embodiments of the methods envisioned herein, the patient-specific device is a surgical patient-specific device. More particularly, the patient-specific device is a guide, implant or prosthesis.

As used throughout the application, the term "guide" refers to a reference structure providing a reference position ensuring the correct axis for applying a surgical tool. In particular, the present application relates to surgical guides for use in determining the axis of one or more surgical tools relative to a body part. A surgical guide can be used during a surgical procedure to help ensure that a surgical instrument or tool is applied to a body part by a practitioner at a particular location and/or with a particular orientation. A guide can have mechanisms providing various degrees of freedom so that the guide can be adjusted in use. Typically, when guiding devices are envisioned, guiding elements are provided on the body structure of the device. Examples of guiding elements include holes, such as drill holes or holes for alignment elements (such as but not limited to K-wires), guiding slots, such as for cutting blades, etc.

In further embodiments of the methods envisioned herein, one or more of the contact surfaces determining the contact of the device with the anatomical part are designed to be patient-specific. More particularly, in such embodiments the surface of the contact element is complementary to the surface of the bone. Accordingly, provided herein are patient-specific surgical, therapeutic or diagnostic devices or guides, comprising a patient-specific surface, the patient-specific surface being complementary to at least part of the body or bone structure of a patient.

In further embodiments, the methods described herein comprise the step of manufacturing said patient-specific device or part thereof through additive manufacturing.

Additive Manufacturing can be defined as a group of techniques used to quickly fabricate a scale model of an object, typically using three-dimensional (3-D) computer aided design (CAD) data of the object. A CAD/CAM manufacturing unit can be adapted for additive manufacturing techniques in order to construct any of the embodiments described herein. Currently, a multitude of Additive Manufacturing techniques is available, including stereo lithography (SLA), Selective Laser Sintering (SLS), Fused Deposition Modeling (FDM), foil-based techniques, etc.

Stereo lithography, presently the most common additive manufacturing technique, utilizes a vat of liquid photopolymer resin to build an object a layer at a time. On each layer, an electromagnetic ray, e.g. one or several laser beams which are computer-controlled, traces a specific pattern on the surface of the liquid resin that is defined by the two-dimensional cross-sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the three-dimensional object to be formed.

Fused deposition modeling (FDM) and related techniques make use of a temporary transition from a solid material to a liquid state, usually due to heating. The material is driven through an extrusion nozzle in a controlled way and deposited in the required place, as described in U.S. Pat. No. 5,141,680.

Foil-based techniques fix coats to one another by means of gluing or photo polymerization or other techniques and cut the object from these coats or polymerize the object.

Typically additive manufacturing techniques start from a digital representation of the 3-D object to be formed, e.g. a guide according to any of the embodiments provided herein. Generally, the digital representation is sliced into a series of cross-sectional layers which can be overlaid to form the object as a whole. The additive manufacturing apparatus uses this data for building the object on a layer-by-layer basis. The cross-sectional data representing the layer data of the 3-D object may be generated using a computer system and computer aided design and manufacturing (CAD/CAM) software. A common feature of such techniques is that objects are typically built layer by layer.

A selective laser sintering (SLS) apparatus is particularly preferred for the manufacture of the surface that is the negative form of a body part (as well as its support) from a computer model. It should be understood, however, that various types of additive manufacturing and tooling may be used for accurately fabricating these surfaces and supports including, but not limited to, stereolithography (SLA), Fused Deposition Modeling (FDM) or milling.

In particular embodiments, at least the patient specific contact surface may be generated by additive or layered manufacturing, e.g. rapid prototype manufacturing techniques directly from medical images of the patient such as X-ray, optical, MRI, PET-scan, CT-scan images or ultrasound images from which a surface can be generated, e.g. by segmentation.

The patient specific surfaces hence have the negative form of a part of the patient's body. In this way these surfaces register with the relevant part of the body, i.e. they are an exact match.

Also the other parts of the patient-specific device can be made through additive manufacturing or layered manufacturing, e.g. rapid prototyping manufacturing techniques using medical images of the patient such as X-ray, optical, MRI, PET-scan, CT-scan images or ultrasound images. For example, the general structure of the patient-specific device and/or the push feature can be manufactured with an additive or layered manufacturing technique such as Rapid Prototyping or other additive fabrication technologies or with classic CNC technologies. The provision of the push feature on the patient-specific device by additive manufacturing further allows the position and orientation of the push feature to reflect the desired orientation of the force. In this way, the push feature can be integrated into the device, which furthers improves stability of the device during the application of a force thereto.

In certain embodiments, the push feature may be a dedicated feature, which implies that it is an additional feature added to the device specifically for the purpose of allowing the accurate application of a force to the device and further does not relate to the actual function of the device on the anatomical part. Examples of dedicated features include handles, bars, finger-pits etc.

It can however be envisioned that the push feature is not a dedicated feature. In particular embodiments, the push feature may be combined with a guiding element of the guide. Indeed, it can be envisioned that in particular embodiments, the optimal location to apply pressure coincides with the required location of a functional feature of the guide (e.g. guide hole or slot). In certain embodiments, the push feature can thus be combined with e.g. a guiding element or screw insertion on the device (e.g. screw hole present in finger pit). In particular embodiments, the push feature will comprise dedicated structural elements which are required for the application of a force to the press-feature.

Also provided herein are patient-specific devices comprising one or more push features as described herein, such as devices obtainable by the methods described herein. The features of the patient-specific devices envisioned herein and more particularly the one or more push feature provided thereon are described hereinabove.

In particular embodiments, improved patient-specific devices are provided herein comprising a body with one or more contact surfaces for positioning on an anatomical part, wherein said body further comprises a dedicated push feature which can be used to apply force onto said patient-specific device, the force being perpendicular to the axis of least-constrained rotational direction and/or parallel to the axis of least-constrained translational direction of the patient-specific device on said anatomical part.

As will be clear to the skilled person, the devices described herein typically comprise a first or "inner" surface with contact surfaces that are envisioned to contact the anatomical part when the device is placed thereon, and a second surface opposite said first surface or "outer" surface, on which the one or more push features are placed. In particular embodiments, one or more of the contact surfaces are patient-specific. This ensures a unique fit of the device on the anatomical part.

In particular embodiments of the improved patient-specific devices described herein, the push feature is a feature specifically designed to receive a hand, such as one or more fingers, more particularly one or more finger-tips. In further particular embodiments, the push feature can be a button, finger-pit, handle, grip, or any other function feature placed on the exterior surface of the body of the device which allows the user to apply force to the patient-specific device.

In particular embodiments, the patient-specific devices envisioned herein are surgical patient-specific devices. More particularly said patient-specific device is a guide. More particularly, where the device is a guide, the body of the patient-specific device further comprises one or more guiding elements or guiding features, for example selected from the list consisting of drill guide, a screw hole and a cutting slot.

In further particular embodiments, the improved patient-specific devices described herein are made by additive manufacturing. More particularly, at least the patient specific contact surface is a surface generated by additive or layered manufacturing, e.g. rapid prototyping manufacturing techniques directly from medical images of the patient such as X-ray, optical, MRI, PET-scan, CT-scan or ultrasound images from which a surface can be generated, e.g. by segmentation. The patient specific surfaces generated by additive manufacturing hence have the negative form of a part of the patient's body. In this way, these surfaces register with the relevant part of the body, i.e. they are an exact match.

In particular embodiments, devices are provided wherein the other parts of the patient-specific device are also made through additive manufacturing or layered manufacturing, e.g. rapid prototyping manufacturing techniques using medical images of the patient such as X-ray, optical, MRI, PET-scan, CT-scan images or ultrasound images as a guide.

In particular embodiments, devices are provided wherein the general structure and/or the push feature is manufactured with an additive or layered manufacturing technique such as Rapid Prototyping or other additive fabrication technologies or with classic CNC technologies.

According to particular embodiments, the devices provided herein are manufactured either in one material or in different materials. Typically, only materials that are biocompatible with the human body are used. Where the device is manufactured using SLS, the device may be fabricated from a polyamide such as PA 2200 as supplied by EOS, Munich, Germany or Duraform PA from 3D Systems, South Caroline, USA, or any other material known by those skilled in the art.

While the envisioned devices and methods have been shown and described with reference to specific embodiments, it will be understood by those skilled in the art that various changes or modifications in form and detail may be made without departing from the scope and spirit of this disclosure.

The devices and methods envisioned herein will be illustrated by the following non-limiting embodiments.

EXAMPLES

Example 1

The present example provides a detailed description of a specific embodiment wherein an envisioned patient-specific device is improved by providing thereon a push feature for accurately positioning said device.

In order to identify the optimal position and orientation of the push feature, the axis of least-constrained direction for rotation and translation must be determined. This is illustrated in FIGS. 1A and 1B.

The present example starts from an existing patient-specific guide. The contact surface (2) of said guide on the anatomical part (1) is identified (see FIG. 2A), and data related to the contact surface may be imported into a computing environment, such as Matlab. The faces of the contact surface (2) are represented by their midpoints with coordinates $r_i$ and unit outward normal vector $n_i$. A wrench vector $w_i$, is created for each of the N different contact points using formula (1).

$$w_i = \begin{bmatrix} n_i \\ n_i \times r_i \end{bmatrix} \quad (1)$$

As the preprocessing phases may result in an irregular triangular mesh, thereby providing different regions on the surface with varying point densities, the addition of a weight factor based on the relative surface s, of the triangle to the equation (1) may be required, resulting in equation 2.

$$w_i = \alpha_i \begin{bmatrix} n_i \\ n_i \times r_i \end{bmatrix} \quad (2)$$

where $$\alpha_i = \sqrt{s_i}$$

These can be combined in a matrix W for all N points resulting in equation (3).

$$W = [w_1 \ w_2 \ \ldots \ w_N] = \begin{bmatrix} X \\ Y \end{bmatrix} \quad (3)$$

The matrix W exists out of two parts, where the matrix X consists of the top 3×N rows of the wrench matrix W, the matrix Y of the lower 3×N rows. The spatial stiffness matrix of this contact surface is then calculated according to equation 4.

$$K = WW' = \begin{bmatrix} X \\ Y \end{bmatrix} [X' \ Y'] = \begin{bmatrix} XX' & XY' \\ YX' & YY' \end{bmatrix} \quad (4)$$

This stiffness matrix has a block-diagonal structure which is used to calculate frame-invariant quality measures for the stability of the contact. The principal translational stiffnesses, $\sigma_i$, (equation 6), are found using the singular values $\sigma_x$ of the matrix (equation 5).

$$X = U_X \sum_X V_X \quad (5)$$

$$\sigma_i = \sigma_X^2 \quad (6)$$

The left singular vectors $U_x$ of the matrix X define the three main directions of translational stability, meaning that the column vector corresponding to the smallest principal translational stiffness represents the least-constrained direction for a translation (4).

The principal rotational stiffnesses, $\mu_i$, (equation 8), are found using the singular values of the matrix ($Y\tilde{V}$) (equation 7), where $\tilde{V}$ consists of the right N×3 columns of the N×N matrix V consisting of the right singular vectors of matrix X.

$$Y\tilde{V} = U_{Y\tilde{V}} \sum_{Y\tilde{V}} V_{Y\tilde{V}} \quad (7)$$

$$\mu_i = (\sigma_{Y\tilde{V}})^2 \quad (8)$$

The principal rotational stiffnesses is scaled by an appropriate factor converting them to the same units as the principal translational stiffnesses, hence being defined an equivalent rotational stiffness $\mu_{eq,i}$ (equation 9).

$$\mu_{eq,i} = \frac{\mu_i}{\rho_{max,i}^2 + (\omega_i \cdot v_i)^2} \quad (9)$$

Figure 2:
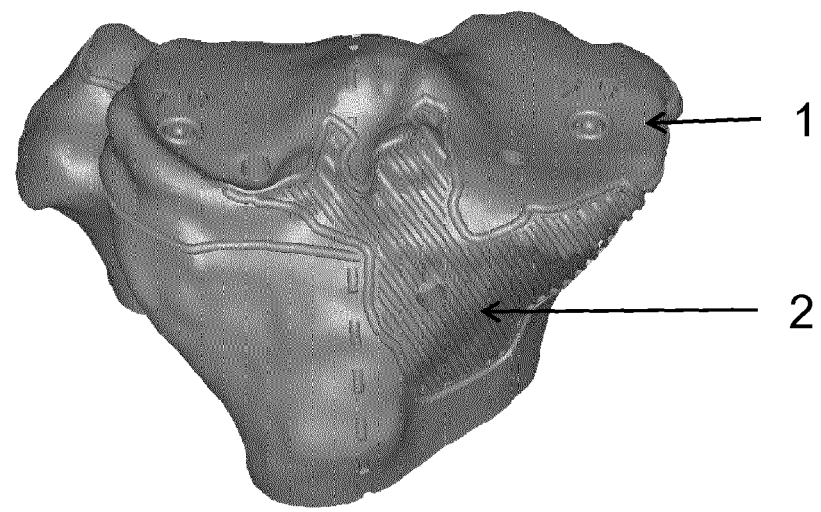
FIG. 2 (A-B): Illustration of the identification of contact surfaces for the design of the patient-specific device according to an embodiment.
Figure 2:
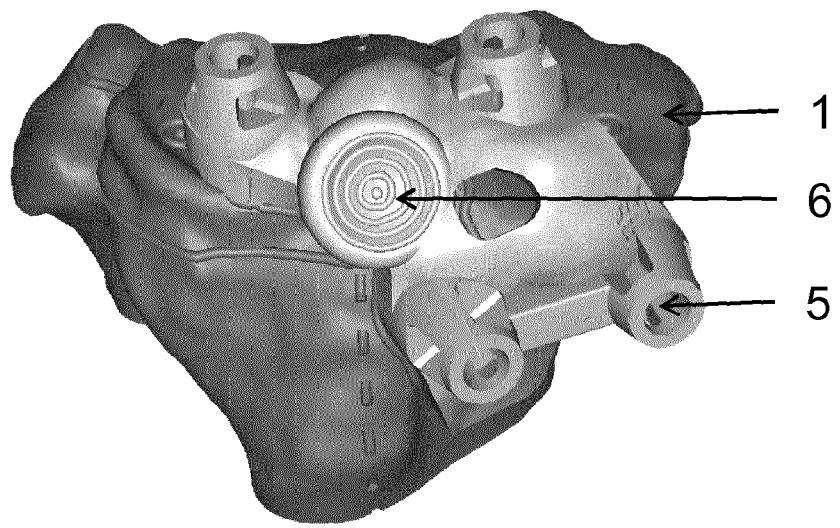

The left singular vectors $U_{Y\tilde{V}}$ of the matrix $Y\tilde{V}$ define the three main directions of rotational stability. The column vector corresponding to the smallest principal (equivalent) rotational stiffness represents the least-constrained direction for rotation (3). Based on the position of the axis of least-constrained rotational direction and/or the axis of least-constrained translational the patient-specific guide (5) is provided with a push feature (6) which ensures that a force applied thereto is perpendicular to the axis of least-constrained rotational direction and/or parallel to the axis of least-constrained translational direction of movement of the patient-specific device on said anatomical part (1) (FIG. 2B).

Example 2

Figure 3:
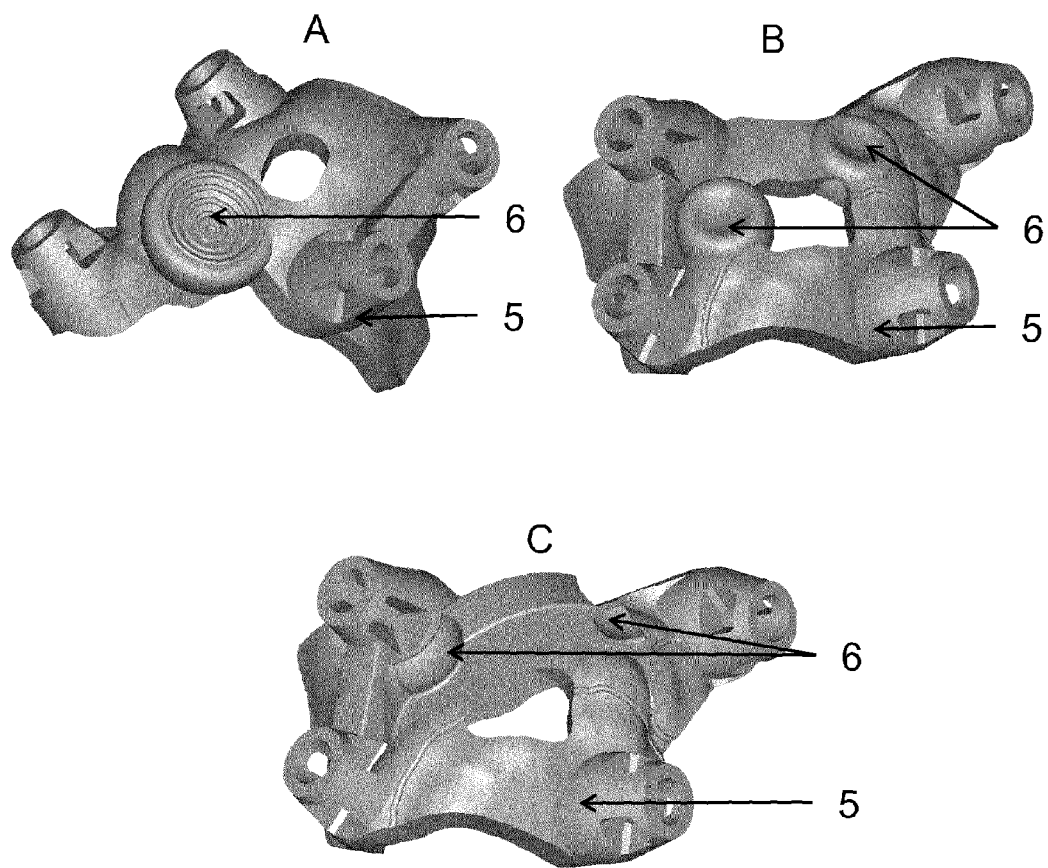
FIG. 3 (A-C): Illustrations of embodiments of patient-specific devices provided with different push features.
Figure 4:
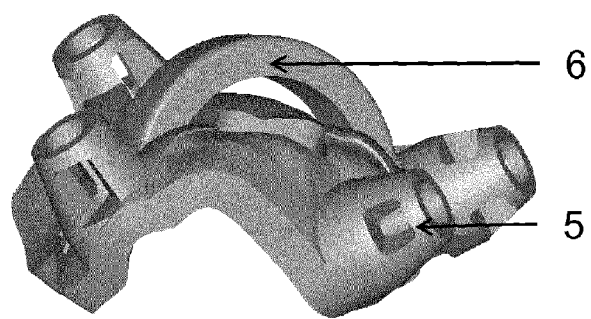
FIG. 4 (A-C): Illustrations of patient-specific devices according to embodiments envisioned herein provided with different types of push features.
Figure 4:
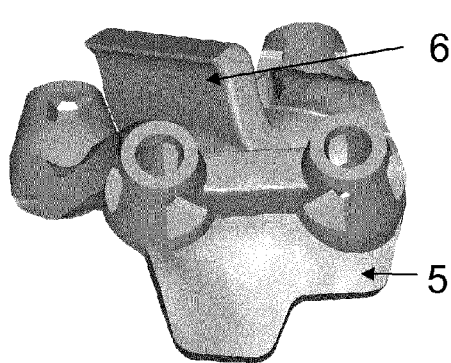
Figure 4:
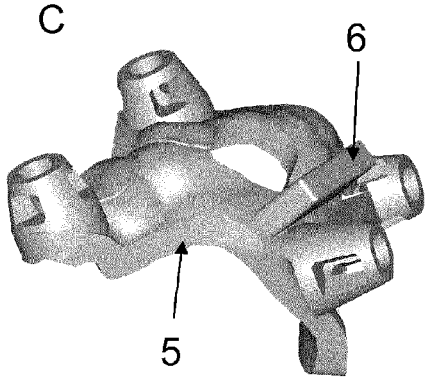

The present example, illustrated by FIGS. 3 and 4, provides various alternative push features that can be provided onto a patient specific device. The push features may for instance be a finger-pit (FIG. 3A), one or more buttons (FIG. 3B), a handle (FIG. 4A), a grip (FIGS. 4B and 4C) or a handle provided with one or more finger pits or buttons (FIG. 3C).

Example 3

Figure 5:
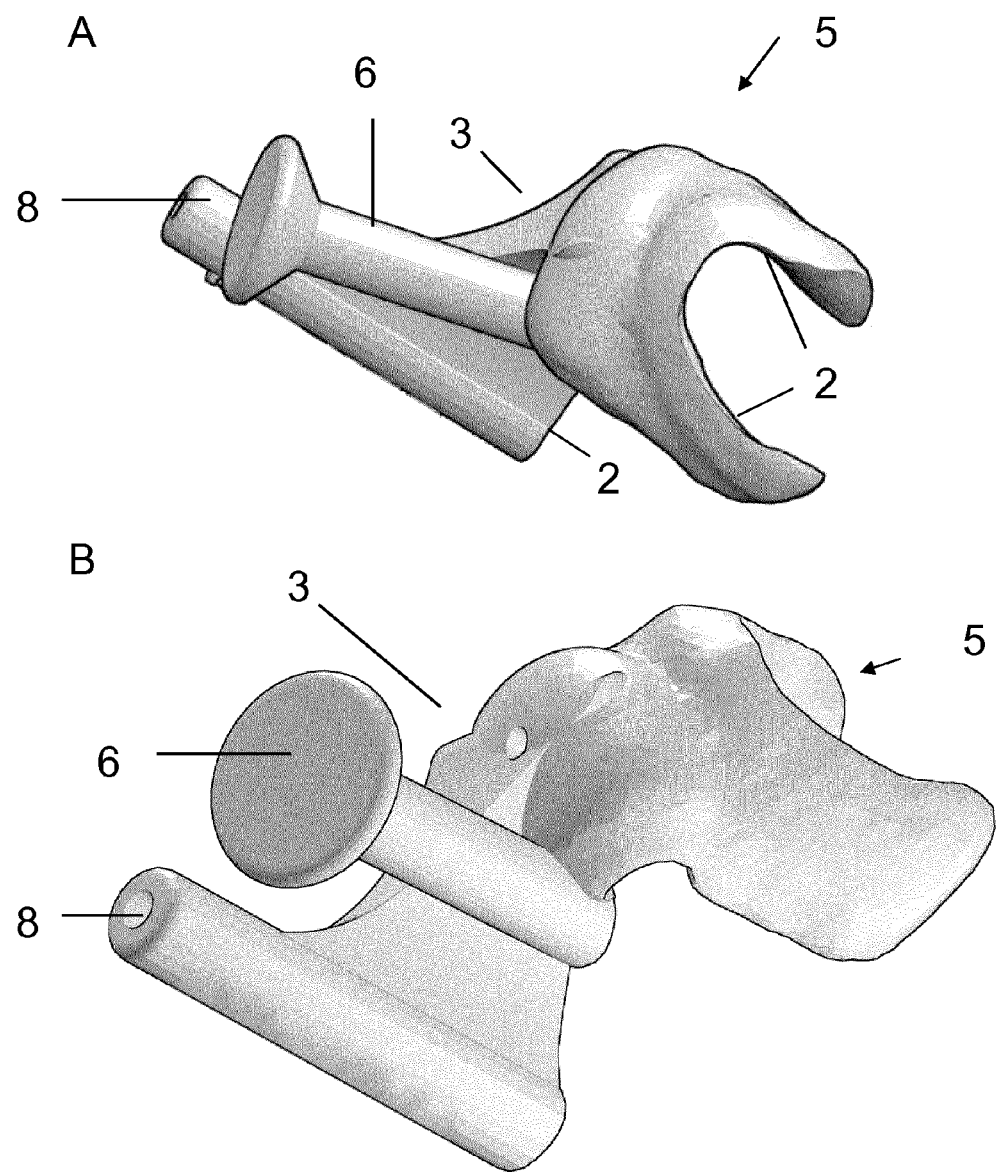
FIG. 5: Illustration of a patient-specific surgical device according to a particular embodiment.
Figure 6:
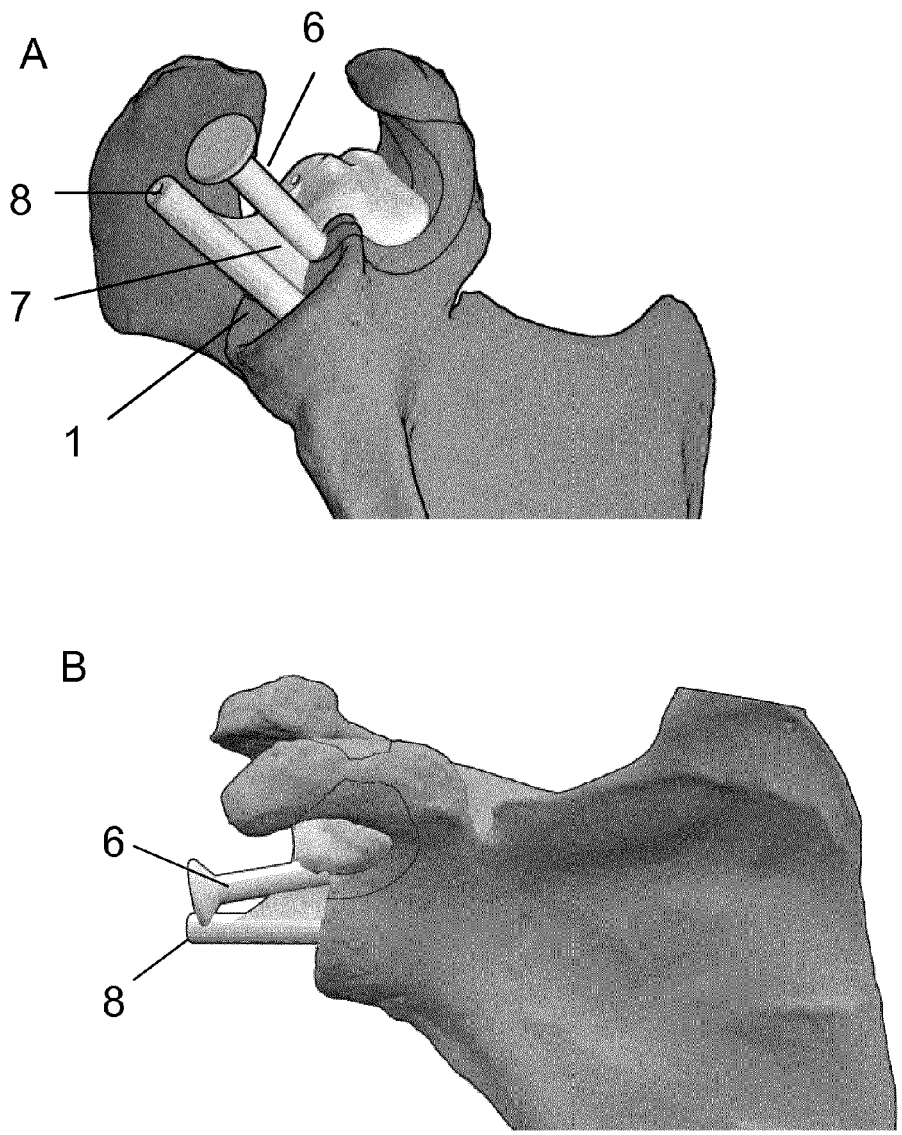
FIG. 6: Illustration of a patient-specific surgical device positioned on the glenoid.

FIGS. 5A and B illustrate a patient-specific device according to particular embodiments. The patient-specific device is a surgical guide for guiding a shoulder surgery, and comprises a support structure (7) and a guiding feature (8), more particularly a drill guide. The surgical guide is intended for positioning onto an anatomical part (1), more particularly a patient's glenoid. Therefore comprises several patient-specific contact surfaces (2) which are at least partially complementary to surfaces on or around a patient's glenoid. FIGS. 6A and B illustrates a shoulder joint, with the patient-specific surgical device (5) positioned on the glenoid (1) via the contact surfaces.

The guide comprises a dedicated push feature (6), more particularly a handle. The orientation and position of the handle facilitates applying a force to the device perpendicular to the axis of least-constrained rotational direction of the guide on the glenoid, parallel to the axis of least-constrained translational direction of the guide on the glenoid, or both. The end of the handle is widened, thus facilitating applying a rotational and/or translational force on the guide via the handle.

Example 4

Defining the Axes by FEA

The present example provides a detailed description of a specific embodiment wherein an envisaged patient-specific device is improved by providing thereon a push feature for accurately positioning said device.

In order to identify the optimal position and orientation of the push feature, this requires determining for said device the axis of least-constrained direction for rotation and translation. One particular method to identify these axes uses finite element analysis (FEA). A set finite element analysis can be performed applying a force onto the patient-specific guide in a plane perpendicular to the axis defining the direction to put the guide onto the patient-specific anatomy. The axis of the force applied will be varied through the different orientations possible within the defined plane. The resulting displacement will be analyzed, thereby identifying which orientation of the force applied results in the largest displacement, thus reflecting the least-constrained axis of translation.

A similar set-up is performed to identify the least-constrained axis of rotation, thereby applying a moment onto the guide positioned on the patient-specific bone where the instantaneous axis of rotation is varied over the orientations perpendicular to the direction to put the guide on the bone and the position of the instantaneous axis of rotation is varied within the bounding box of the contact surface. The resulting rotation will be analyzed, thereby identifying which position and orientation of the instantaneous axis of rotation used to apply a moment onto the guide results in the largest rotation, reflecting the least-constrained axis of rotation.

Example 5

Alternative Method for Example 1

The present example provides a detailed description of a specific embodiment wherein an envisioned patient-specific device is improved by providing thereon a push feature for accurately positioning said device.

In order to identify the optimal position and orientation of the push feature, this requires determining for said device the axis of least-constrained direction for rotation and translation. This is illustrated in FIGS. 1A and 1B.

The present example starts from an existing patient-specific guide. The contact surface (2) of said guide on the anatomical part (1) is identified first. The faces of the contact surface (2) are represented by their vertices with coordinates $r_i$ and unit outward normal vector $n_i$. A wrench vector $w_i$ is created for each of the N different contact points using formula (1b).

$$w_i = \begin{bmatrix} n_i \\ n_i \times r_i \end{bmatrix} \quad (1b)$$

These can be combined in a matrix W for all N points resulting in equation (2b).

$$W = [w_1 w_2 \ldots w_N] \quad (2b)$$

The spatial stiffness matrix of this contact surface is then calculated according to equation (3b).

$$K = WW^T = \begin{bmatrix} A & B \\ B^T & D \end{bmatrix} \quad (3b)$$

This stiffness matrix has a block-diagonal structure which is used to calculate frame-invariant quality measures for the stiffness of the contact. The principal translational stiffnesses, $\sigma_i$, (equation 6b), are found using the eigenvalues $\sigma_x$ of the submatrix A (equation 5b).

$$A = U_A \Lambda_A U_A^{-1} \quad (5b)$$

$$\lambda_i = \sigma_{x,i} \quad (6b)$$

The left singular vectors $U_A$ of the matrix A define the three main directions of translational stability, meaning that the column vector corresponding to the smallest principal translational stiffness represents the least-constrained direction for a translation (4).

The principal rotational stiffnesses, $\mu_i$, (equation 8b), are found using the singular values of the matrix $K_V$ (equation 7b).

$$K_V = D - BA^{-1}B^T = U_{K_V}\Lambda_{K_V}U_{K_V}^T \quad (7b)$$

$$\mu_i = \lambda_{K_V,i} \quad (8b)$$

The principal rotational stiffnesses are scaled by an appropriate factor converting them to the same units as the principal translational stiffnesses, hence being defined an equivalent rotational stiffness $\mu_{eq,i}$ (equation 9b).

$$\mu_{eq,i} = \frac{\mu_i}{\rho_{max,i}^2 + (\omega_i \cdot v_i)^2} \quad (9b)$$

The left singular vectors $U_{K_V}$ of the matrix $K_V$ define the three main directions of rotational stability. The column vector corresponding to the smallest principal (equivalent) rotational stiffness represents the least-constrained direction for rotation (3). Based on the position of the axis of least-constrained rotational direction or orientation of the axis of least-constrained translation the patient-specific guide is provided with a push feature to ensure that a force applied thereto is perpendicular to the axis of least-constrained rotational direction or parallel to the axis of least-constrained translational direction of movement of the patient-specific device on said anatomical part.

What is claimed is:

1. A method for providing a patient-specific device for placement on a patient's anatomical part, the method comprising the steps of:
    determining one or more areas on the anatomical part that can be used for the design of one or more contact surfaces on a patient-specific device configured to be placed on the anatomical part;
    determining, based on the one or more contact surfaces, an axis of least-constrained rotational direction of the patient-specific device on the anatomical part, an axis of least-constrained translational direction of the patient-specific device on the anatomical part, or both; and
    designing the patient-specific device with one or more contact surfaces and one or more push features that can be used for applying force onto the patient-specific device;
    wherein the one or more push features are designed such that a force applied thereto is perpendicular to the axis of least-constrained rotational direction of movement of the patient-specific device on the anatomical part, parallel to the axis of least-constrained translational direction of movement of the patient-specific device on the anatomical part, or both.

2. The method according to claim 1, wherein the push feature is a button, finger-pit, handle or grip.

3. The method according to claim 1, wherein the push feature is spring-loaded, which is reactive to a predetermined pressure applied thereto.

4. The method according to claim 1, wherein the patient-specific device is provided with two or more push features.

5. The method according to claim 1, wherein the patient-specific device is a surgical patient-specific device.

6. The method according to claim 1, wherein the patient-specific device is a guide, prosthesis or implant.

7. The method according to claim 1, wherein one or more of the contact surfaces are patient-specific.

8. The method according to claim 1, further comprising: manufacturing the patient-specific device or part thereof through additive manufacturing.

9. The method according to claim 8, wherein the additive manufacturing comprises one of stereo lithography, selective laser sintering, or fused deposition modeling.

10. The method according to claim 1, further comprising: generating a three-dimensional model of the patient's anatomical part.

11. The method according to claim 10, wherein the three-dimensional model of the patient's anatomical part is based on at least one of: an X-ray image, a magnetic resonance image, a computed tomography scan image, a positron emission tomography scan image, or an ultrasound image of the patient's anatomical part.

12. The method according to claim 1, wherein the axis of least-constrained rotational direction of the patient-specific device on the anatomical part, the axis of least-constrained translational direction of the patient-specific device on the anatomical part, or both, are determined using a finite element analysis.

13. The method according to claim 12, further comprising: generating a stiffness matrix based on at least one of a translational parameter or a rotational parameter determined using the finite element analysis.

14. The method according to claim 1, further comprising: designing the patient-specific device with one or more guiding elements.

15. The method according to claim 14, wherein at least one of the one or more guiding elements comprises a hole or a guiding slot.

* * * * *